(12) United States Patent
Mai

(10) Patent No.: US 11,103,253 B2
(45) Date of Patent: Aug. 31, 2021

(54) EMBOLIZATION SCAFFOLD DEVICES

(71) Applicant: MedStar Health, Washington, DC (US)

(72) Inventor: Jeffrey Mai, Arlington, VA (US)

(73) Assignee: MEDSTAR HEALTH, Washington, DC (US)

( * ) Notice: Subject to any disclaimer, the term of this patent is extended or adjusted under 35 U.S.C. 154(b) by 99 days.

(21) Appl. No.: 16/377,437

(22) Filed: Apr. 8, 2019

(65) Prior Publication Data

US 2019/0307457 A1 Oct. 10, 2019

Related U.S. Application Data

(60) Provisional application No. 62/655,461, filed on Apr. 10, 2018.

(51) Int. Cl.
*A61B 17/12* (2006.01)

(52) U.S. Cl.
CPC .... *A61B 17/12113* (2013.01); *A61B 17/1214* (2013.01); *A61B 17/12031* (2013.01); *A61B 17/12172* (2013.01); *A61B 2017/1205* (2013.01)

(58) Field of Classification Search
CPC .......... A61N 17/12113; A61N 17/1214; A61N 17/12031; A61N 17/12172; A61N 17/1205; A61N 2017/1205; A61N 17/1204; A61N 17/12109; A61N 2017/3484; A61N 2017/3488; A61N 17/12099; A61N 17/12118; A61N 17/12104; A61M 25/04; A61M 25/06; A61M 2025/0293; A61M 2025/0233; A61L 2430/36; A61F 6/20; A61F 6/22; A61F 6/225
See application file for complete search history.

(56) References Cited

U.S. PATENT DOCUMENTS

| | | | |
|---|---|---|---|
| 5,911,731 | A | 6/1999 | Pham et al. |
| 5,916,235 | A | 6/1999 | Guglielmi |
| 5,935,148 | A | 8/1999 | Villar et al. |
| 6,093,199 | A | 7/2000 | Brown et al. |
| 6,168,615 | B1 | 1/2001 | Ken et al. |
| 6,375,668 | B1 | 4/2002 | Gifford et al. |
| 8,262,692 | B2 | 9/2012 | Rudakov |

(Continued)

FOREIGN PATENT DOCUMENTS

| | | |
|---|---|---|
| WO | 99/56636 A1 | 11/1999 |
| WO | 2008/151204 A1 | 12/2008 |
| WO | 2017/221252 A1 | 12/2017 |

OTHER PUBLICATIONS

PCT International Search Report and Written Opinion for corresponding International Application Serial No. PCT/US2019/026274, dated Jul. 2, 2019, pp. 1-15.

*Primary Examiner* — Tan-Uyen T Ho
*Assistant Examiner* — Bridget E. Rabaglia
(74) *Attorney, Agent, or Firm* — Tarolli, Sundheim, Covell & Tummino LLP

(57) ABSTRACT

An embolization scaffold device. The scaffold has a base having a central longitudinal axis extending therethrough and a plurality of expandable struts extending from the base. Each of the struts has a proximal portion extending from the base and substantially aligned with the central longitudinal axis, an intermediate arcuate portion radially extending away from the central longitudinal axis, and a distal portion curving back towards the central longitudinal axis.

13 Claims, 14 Drawing Sheets

(56) References Cited

U.S. PATENT DOCUMENTS

| | | |
|---|---|---|
| 9,468,442 B2 | 10/2016 | Huynh et al. |
| 9,968,432 B2 * | 5/2018 | Lagodzki ......... A61B 17/12145 |
| 2003/0199919 A1 * | 10/2003 | Palmer ............. A61B 17/12172 |
| | | 606/200 |
| 2006/0106421 A1 | 5/2006 | Teoh |
| 2010/0069948 A1 | 3/2010 | Veznedaroglu et al. |
| 2014/0343602 A1 | 11/2014 | Cox et al. |
| 2015/0005810 A1 | 1/2015 | Center et al. |
| 2015/0238199 A1 | 8/2015 | Le et al. |
| 2015/0313605 A1 | 11/2015 | Griffin |
| 2019/0021741 A1 * | 1/2019 | Chen ................ A61B 17/12177 |

* cited by examiner

EMBOLIZATION SCAFFOLD DEVICES

CROSS-REFERENCE TO RELATED APPLICATIONS

The present application claims priority to U.S. Provisional Application No. 62/655,461, filed on Apr. 10, 2018, the entirety of which is incorporated by reference herein.

TECHNICAL FIELD

The present disclosure relates to embolization scaffolds that can be used in conjunction with embolization coils to occlude an aneurysm or vascular malformation emerging from a blood vessel.

BACKGROUND

Intravascular interventional procedures for providing an artificial embolism are desirable in some patients for controlling internal bleeding, preventing blood supply to tumors or vascular malformations, or relieving pressure in the vessel wall near an aneurysm. Several approaches are known for providing an artificial embolism, including the use of an inflatable, detachable balloon or the injection of a coagulative substance. Another approach utilizes an occlusive wire coil and delivery system for positioning the coil at a desirable site in a blood vessel. Regarding the latter approach, an embolization coil is typically delivered to a desired location in the vasculature of a patient through the use of a catheterization procedure. In this procedure, a catheter is inserted into the vasculature of a patient and positioned to be proximal to the desired or targeted location. Then a coil is loaded into the lumen of the catheter and advanced through the catheter using a "push" rod until it reaches and exits through the distal end of the catheter. Other techniques to deploy coils involve electrical, chemical or hydraulic release systems. Upon depositing within the aneurysm, the cons expand and initiate a thrombotic reaction within the aneurysm. If successful, this can prevent bleeding from the aneurysm. In the case of broad-based aneurysms, a stent may be passed first into the parent artery to serve as a scaffold for the coils.

Many embolization devices for aneurysms are rigid devices with limited compliance. Accordingly, such devices can be difficult to deliver to an aneurysm with an oblique take off, may require custom or large-bore microcatheters to cannulate aneurysms, and may have an increased risk of deployment in ruptured aneurysms.

SUMMARY

The present disclosure provides an embolization scaffold device (also referred to herein as a "scaffold") for occluding a blood vessel to create an embolus or thrombosis in the blood vessel. A scaffold can provide enhanced protection at the neck of an aneurysm to allow for complete obliteration of the aneurysm and can minimize the risk of rupture by reducing transmural wall pressure during deployment. A scaffold can be used in conjunction with an integrated in-line embolization coil to facilitate a single-step, single-device obliteration of aneurysms or used with an adjunctive coil to treat broad-based as well as saccular aneurysms with enhanced protection at the aneurysm neck. A scaffold does not require dual-antiplatelet therapy and is therefore broadly applicable to both ruptured and unruptured aneurysms. A scaffold can also conform to the shape of a myriad of aneurysmal shapes.

An embolization scaffold device can retain an embolization coil in position within an aneurysm and can be re-sheathed or re-deployed if the scaffold is not placed in the correct location initially. Contrary to other embolization devices, scaffolds as described herein have a low-profile, flexible design that can allow for ready microcatheterization into aneurysms with difficult aneurysm takeoffs, distal aneurysm branch positions, and varying morphologies. Scaffolds as described herein do not necessarily require a custom delivery microcatheter.

As mentioned above, in certain embodiments, an embolization coil is integrated in-line with a scaffold. Such an embolization coil can have a complex shape sized to the length of struts of a scaffold. This facilitates single-step, single-device obliteration of aneurysms to accelerate safe treatment of aneurysms whether ruptured or un-ruptured. An embolization coil is free to seek and obliterate surrounding aneurysmal space in between the struts of a scaffold, given the open design of such a scaffold. Any loops of an embolization coil can be retained in an aneurysm, such as a broad-based aneurysm, by the distal portion and/or the distal ends of the struts of the scaffold.

BRIEF DESCRIPTON OF DRAWINGS

DETAILED DESCRIPTION

The present disclosure relates to methods and devices for occluding a blood vessel to create an embolus in the blood vessel and treat vascular malformations or disease. For example, the present invention provides embolization scaffolds, embolization kits that include scaffolds and embolization coils, embolization systems that include scaffolds that are operably coupled to embolization coils, and methods of delivering embolization scaffold systems.

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. It will be understood that when an element is referred to as being "over," "on," "attached" to, "connected" to, "coupled" with, "contacting," "in communication with," etc., another element, it can be directly over, on, attached to, connected to, coupled with, contacting, or in communication with the other element or intervening elements may also be present. In contrast, when an element is referred to as being "directly over," "directly on," "directly attached" to, "directly connected" to, "directly coupled" with, "directly contacting," or in "direct communication" with another element, there are no intervening elements present. An element that is disposed "adjacent" another element may have portions that overlap or underlie the adjacent element. By "substantially" is meant that the shape, configuration, or orientation of the element need not have the mathematically exact described shape, configuration or orientation but can have a shape, configuration or orientation that is recognizable by one skilled in the art as generally or approximately having the described shape, configuration, or orientation. The embolization scaffold devices are used for medical purposes and therefore are sterile.

Figure 1:
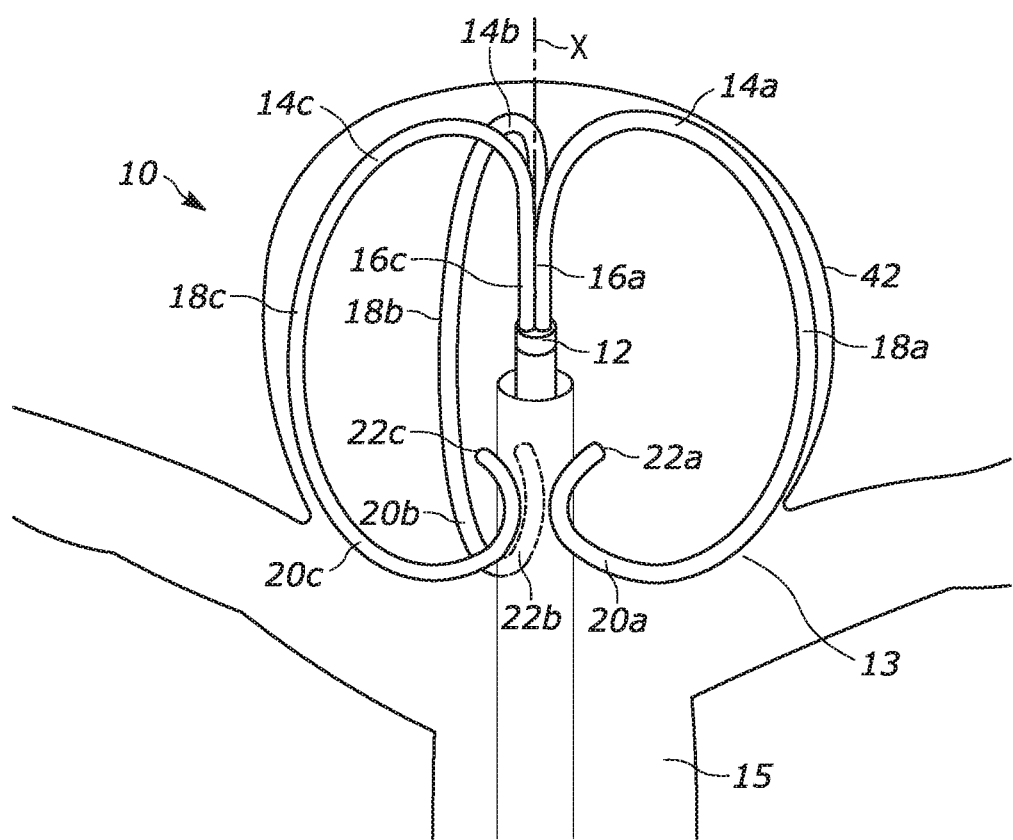
FIG. 1 is a perspective view of an embolization scaffold device disposed in a saccular aneurysm according to an embodiment of the present disclosure.
Figure 2:
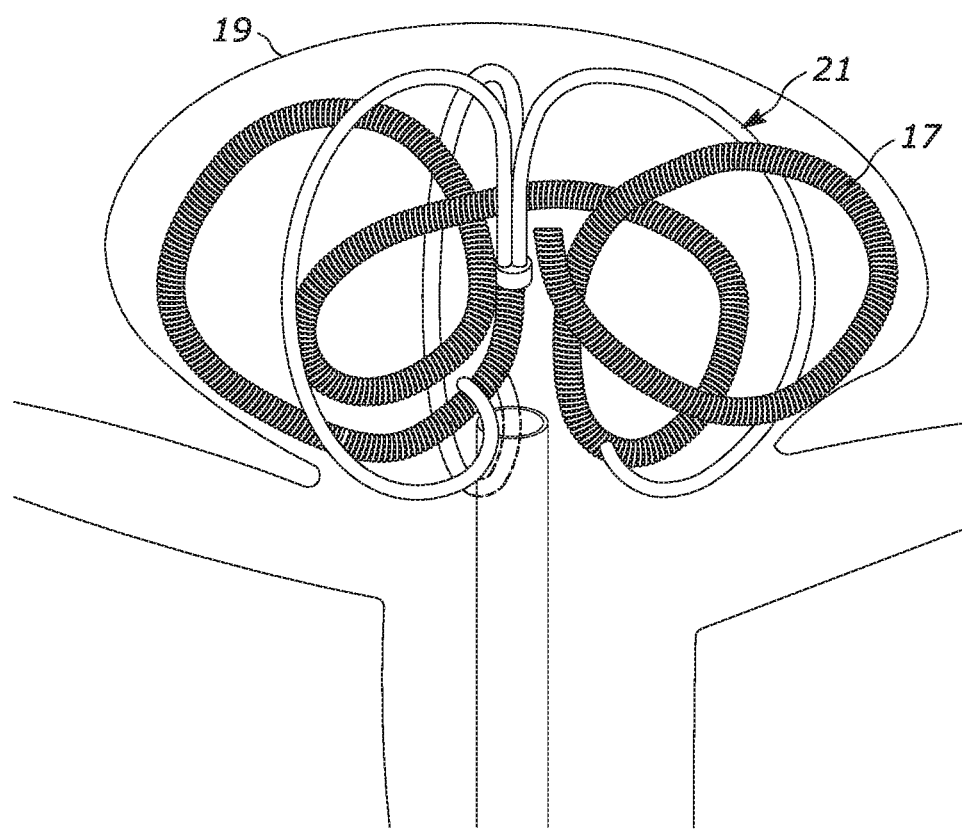
FIG. 2 is a perspective view of an embolization scaffold device and embolization coil disposed in a broad-based aneurysm according to an embodiment of the present disclosure.

Referring to FIG. 1, an expandable embolization scaffold device 10 can comprise a base 12 having a central longitudinal axis X extending therethrough. Embolization scaffold device 10 can further include a plurality of struts 14. Each strut 14 can have a proximal portion 16 extending from base 12 and substantially aligned with central longitudinal axis X, an intermediate arcuate portion 18 radially extending away from central longitudinal axis X, and a distal portion 20 curving back towards central longitudinal axis X. The outer surfaces of the intermediate arcuate portion of the struts can face the inner surface of the aneurysm 42 in a deployed expanded configuration and can apply a radial outward force to stabilize the scaffold against the aneurysm wall. Further, the intermediate arcuate portion can be flexible enough to substantially conform to the shape of the inner surface of the aneurysm. Distal portion 20 curving inward can provide scaffold coverage at the aneurysm base 13 to protect a subsequently delivered embolization coil from herniating outward into the parent vessel 15. In certain embodiments, each strut 14 can also have a distal terminal end 22 that curves away from central longitudinal axis X towards intermediate arcuate portion 18 of respective strut 14. Such terminal ends that curve inward can support embolization coils at the neck of aneurysms, such as broad-based aneurysms. By curving inward, the terminal ends of the struts are not constrained at the aneurysm neck and can automatically adjust themselves to an aneurysm neck having various diameters (e.g. if the neck proves smaller than anticipated, the terminal ends of the struts can simply overlap at the neck, which is not possible if the struts are joined to a central strut or base at two location). By extension and with reference to FIG. 2, an adjunctive coil 17 deposited in an aneurysm 19 and retained at least partially within a scaffold 21 can be less constrained by scaffold 21 and can seek out space within irregularly shaped aneurysms (e.g. not perfectly spherical). The scaffold is primarily designed to retain a coil at the aneurysm neck, but above the neck, the coil is freer to conform to the particular shape of the aneurysm. In other words, since the struts have minimal coverage along the body of the aneurysm, except at the apex and at the neck of the aneurysm, an embolization coil deployed within the scaffold is not significantly constrained by the device and can "seek" space within the aneurysm to enhance aneurysmal obliteration yet avoid herniation into the parent vessel because of the inwardly curved distal portion of the scaffold as depicted in FIG. 2. The unconstrained nature of the scaffold struts means that the scaffold can more readily accommodate irregular shaped aneurysms, such as ellipsoid or eccentric shapes as illustrated in FIG. 2. Embolization scaffold devices 10 and 21 are illustrated in FIG. 1 and FIG. 2 and the remaining figures as being placed in an aneurysm but the scaffold could be placed in other areas of a blood vessel where embolization is desired.

The expandable embolization scaffold device can assume an un-expanded and an expanded configuration. For example, the embolization scaffold device can be fabricated from a shape memory material such as nitinol and resume a pre-determined shape in an expanded configuration or another flexible material. Alternatively, the embolization scaffold device can be expanded by an expandable member such as a balloon or other inflatable or expandable device. The terminal distal ends of the expandable embolization scaffold device can comprise a flexible material and are therefore not constrained at the aneurysm neck allowing the scaffold to conform to irregular, eccentric and wide aneurysm necks as depicted in FIG. 2. Other portions of the scaffold can also be flexible so that the struts of the scaffold can more readily be compressed into a delivery catheter as device stiffness is a major impediment to placing such devices in aneurysms with complex anatomy. A delivery microcatheter should be able to navigate into an aneurysm with minimal resistance and kick-back and further deploy the scaffold with mechanics that minimize manipulation of the microcatheter. This can be relevant in small aneurysms, ruptured aneurysms, and aneurysms with acute takeoffs from the parent vessel. The design of an embolization scaffold device can reduce the amount of material mass (such as metal mass) in the scaffold so that the scaffold can navigate to the aneurysm and be easily deployed with a minimal amount of resistance and kick-back.

Figure 3:
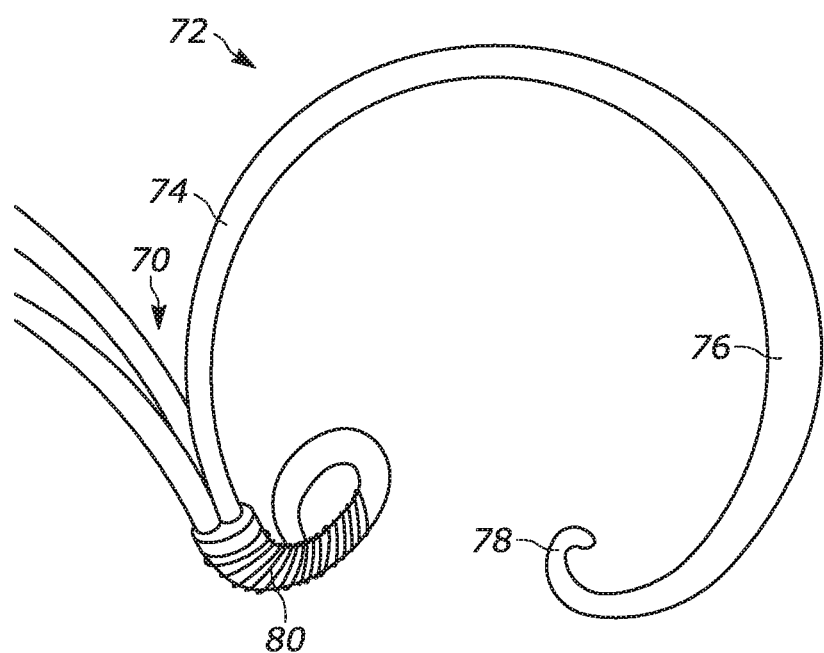
FIG. 3 is an enlarged side view of a strut of an embolization scaffold device according to an embodiment of the present disclosure.

FIG. 3 is an enlarged view of an embodiment of a strut 72 of an embolization scaffold device 70 attached to an embolization coil 80. Strut 72 can be fabricated from a shape memory material that allows it to be "unfurled" to its predetermined shape when deployed. Strut 70 can have varying resistance/compliance along its length to appose aneurysmal walls and still provide support for embolization coils to obliterate the aneurysmal space. For example, strut 72 can have a proximal armature 74, a distal armature 76, and a distal end 78. Proximal armature 74 can be more flexible than distal armature 76 to allow compliance with the aneurysm inner wall. Distal armature 76 can be more rigid than proximal armature 74 to support the mass of embolization coil 80 when both the embolization scaffold device 70 and coil 80 are in a final deposited position in the aneurysm. Distal end 78, which curves inward, can be the softest portion of strut 72 to allow strut 72 to track the aneurysmal dome wall. Furthermore, strut 72 can be radio-opaque for clear visualization during deployment. Although the above description is with respect to a single strut, the other struts of the plurality of struts of an embolization scaffold device can have similar properties.

Although an embolization scaffold device has more than two struts, in certain embodiments, an embolization scaffold device can have a minimum of three struts to stabilize the device within the aneurysm. For example, FIG. 1 depicts an embolization scaffold device with three struts such as a central strut 14b disposed substantially equidistant from two lateral struts 14a and 14c. Such a trefoil configuration can reduce wall stress of the aneurysm by distributing pressure across all three struts of the embolization scaffold device. This can be relevant when treating ruptured aneurysms and to minimize the risk of aneurysm perforation and rupture when subsequently delivering an embolization coil into the aneurysm.

Figure 4:
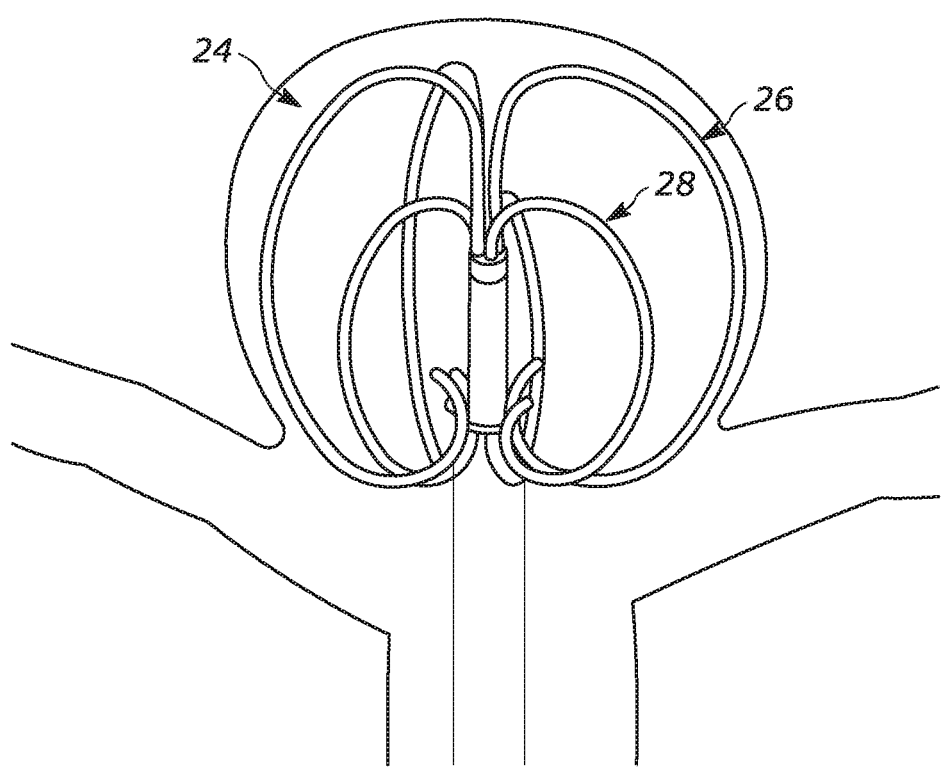
FIG. 4 is a perspective view an embolization scaffold device disposed in an aneurysm according to an embodiment of the present disclosure.

Referring to FIG. 4, in certain embodiments, an embolization scaffold device 24 can comprise a mult-tier scaffold. In particular, embolization scaffold device 24 can comprise a first set of struts 26 and a second set of struts 28 with the second set of struts located proximal to the first set of struts 26. In the case of two sets of struts, the second set of struts can be axially offset from the central axis of the first set of struts by approximately 60 degrees. Although FIG. 4 only illustrates two tiers of struts, the embolization scaffold device can comprise more than two tiers of struts. Such multi-tier struts can increase the coverage of a single embolization scaffold in the aneurysm, stabilize the device in the aneurysm, and improve support at the neck of the aneurysm.

Figure 5:
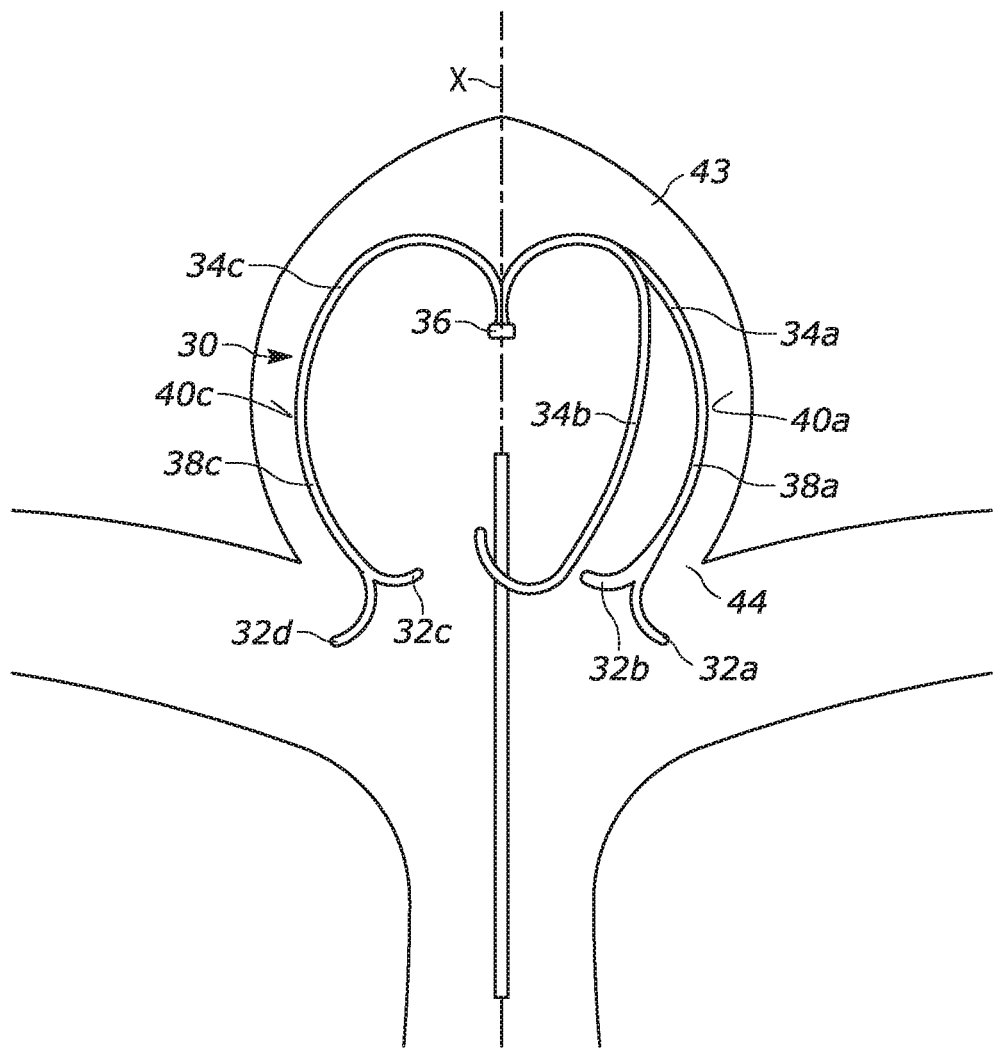
FIG. 5 is a perspective view an embolization scaffold device disposed in an aneurysm according to an embodiment of the present disclosure.

Referring to FIG. 5, in certain embodiments, an embolization scaffold device 30 can comprises one or more tines at the distal end of the scaffold. In particular, at least one of the plurality of struts 34 comprises a tine 32 located at a distal end thereof. Tine 32 is oriented in a direction away from the central axis X of base 36. FIG. 4 illustrated two tines 32 located at the respective distal end of struts 34a and 34c. The outer surfaces 38a and 38c of struts 34a and 34c face the inner surface 40a and 40b of aneurysm 43 and can apply a radial outward force to stabilize the scaffold against the aneurysm wall as described above. As illustrated in FIG. 5, tines 32 can serve as anchors to brace embolization scaffold device 30 against the inlet 44 of aneurysm 43 and as such can enhance stability of the scaffold in aneurysms, such as broad-based aneurysms. Embolization scaffold device 30 however is still able to be recovered from the aneurysm after deployment if necessary.

Figure 6A:
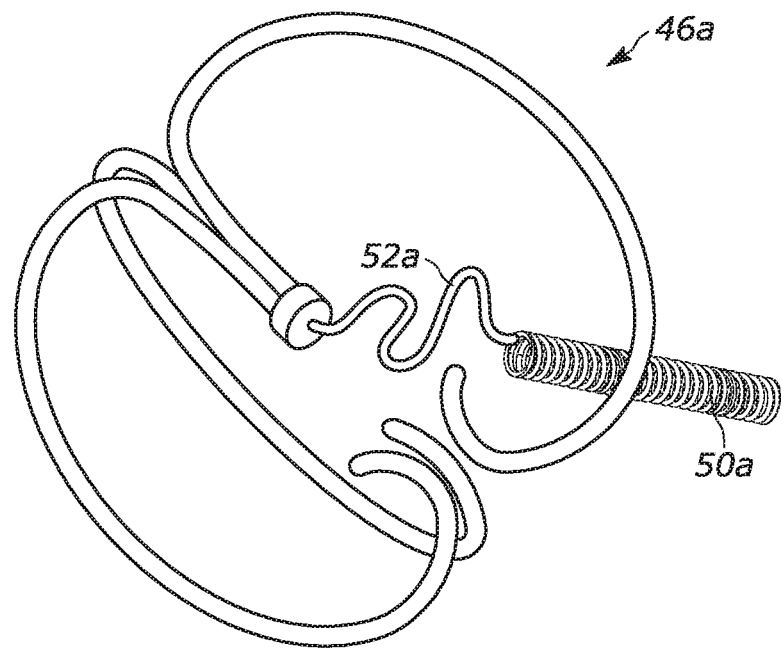
FIGS. 6A to 6C are perspective views of different embodiments of an embolization scaffold device operably coupled to an embolization coil according to the present disclosure.
Figure 6B:
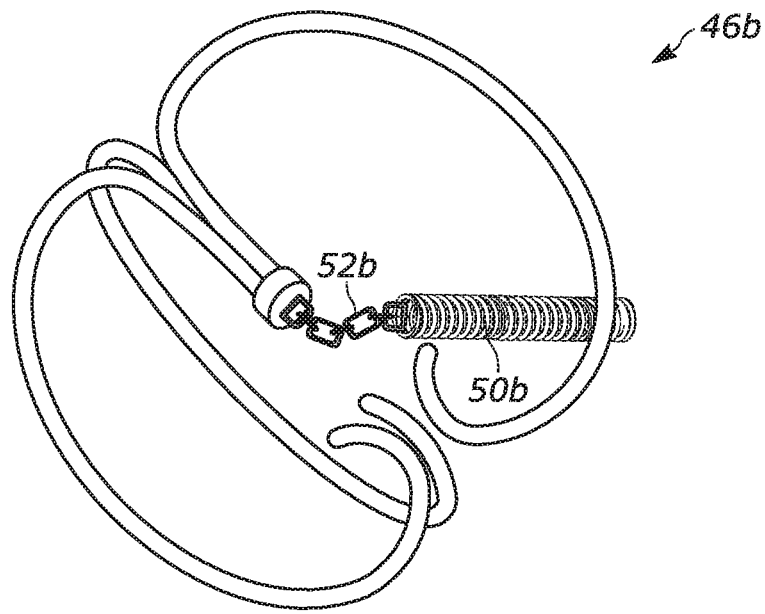
Figure 6C:
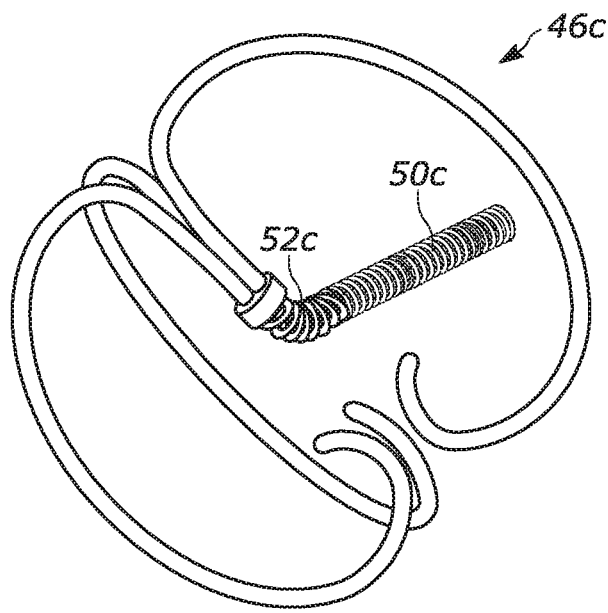

In certain aspects, the present disclosure provides embolization kits including any one or more of the embolization scaffold devices described above and a separate adjunctive embolization coil unattached to the embolization scaffold device. In other aspects, embolization systems are provided that include any one or more of the embolization scaffold devices described above operably coupled to an embolization coil. For example, referring to FIG. 6A to 6C, an embolization scaffold device 46 can be attached to an embolization coil 50 by a flexible linker 52. As shown in FIG. 6A, linker 52a can be a filament such as a wire. Alternatively, linker 52b can be a chain as shown in FIG. 6B or linker 52c can be a spring or soft coil as shown in FIG. 6C. As illustrated in FIG. 3, embolization coil 80 can be a custom-sized coil that can be sized to be in-line with the embolization scaffold device 70. Whether as part of a system or a kit, the embolization coil can have a variety of shapes such as a helically wound coil, a randomly wound coil, coils wound within coils, or other coil configurations.

Figure 7:
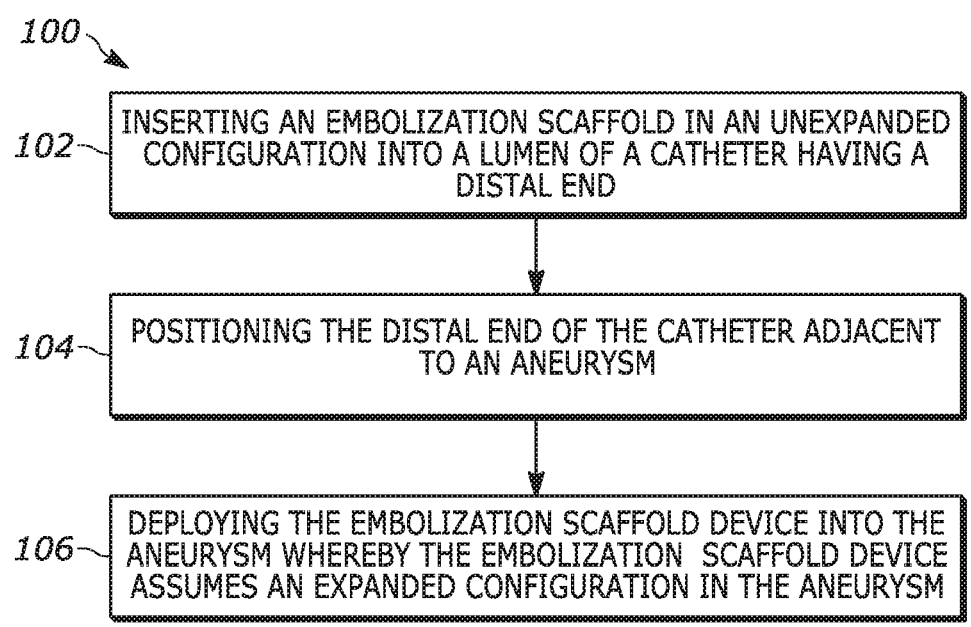
FIG. 7 is a flowchart depicting steps of a method of delivering an embolization scaffold device according to an embodiment of the present invention.

In other aspects, the present disclosure provides a method of delivering an embolization system into an aneurysm. Referring to FIG. 7, method 100 comprises inserting an embolization scaffold device in an unexpanded configuration into a lumen of a catheter having a distal end 102. The embolization scaffold device comprises a base having a central longitudinal axis extending therethrough, a plurality of struts each having a proximal portion extending from the base and substantially aligned with the central longitudinal axis, an intermediate arcuate portion radially extending away from the central longitudinal axis, and a distal portion curving back towards the central longitudinal axis. The method further includes positioning the distal end of the catheter adjacent to an aneurysm 104. Method 100 then comprises deploying the embolization scaffold device into the aneurysm whereby the embolization scaffold device assumes an expanded configuration in the aneurysm 106. An embolization coil can then be deposited into the aneurysm and can be retained in position at least partially within the embolization scaffold device.

Figure 8A:
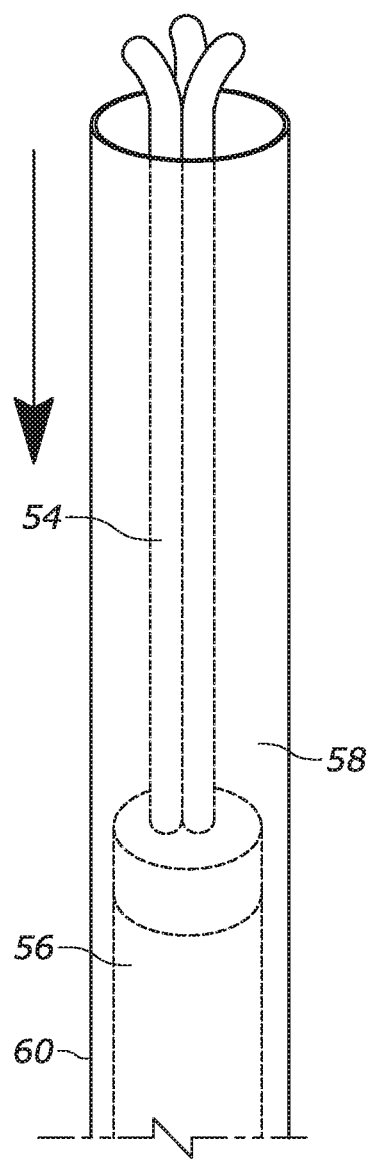
FIGS. 8A-8C are schematic illustrations depicting steps of a method of deploying an embolization scaffold device according to an embodiment of the present disclosure.
Figure 8B:
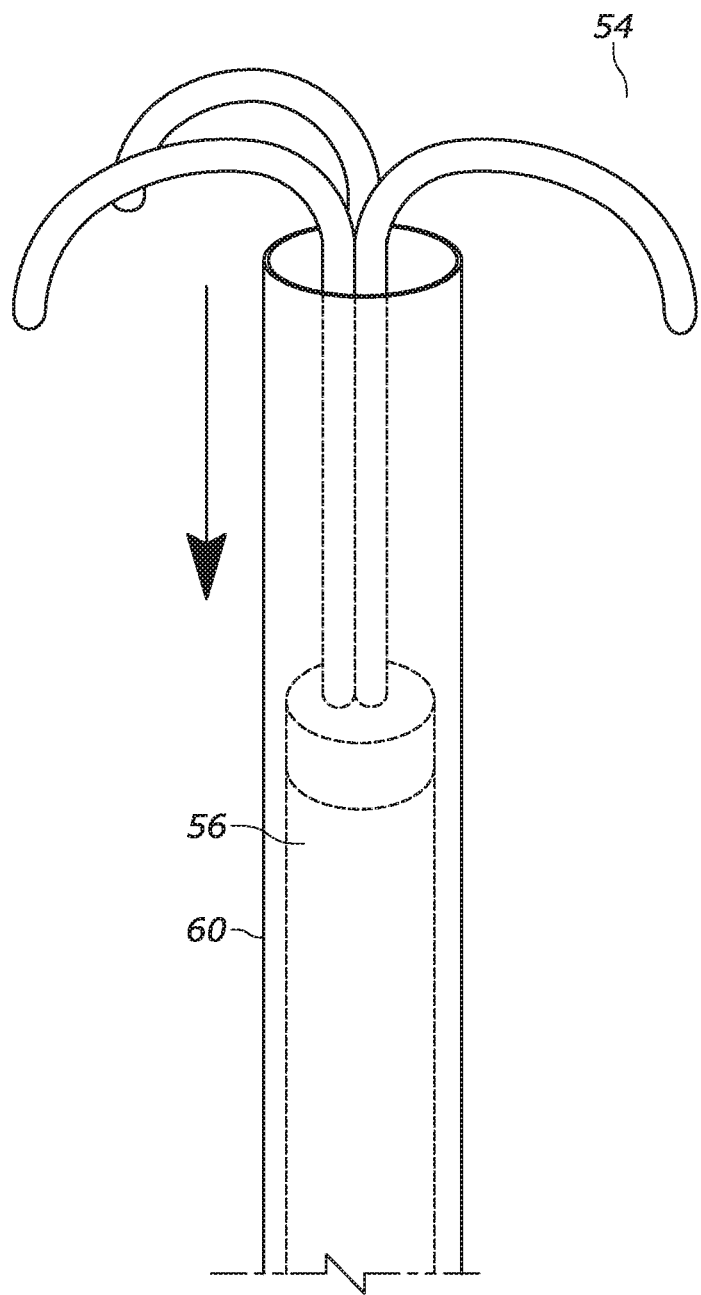
Figure 8C:
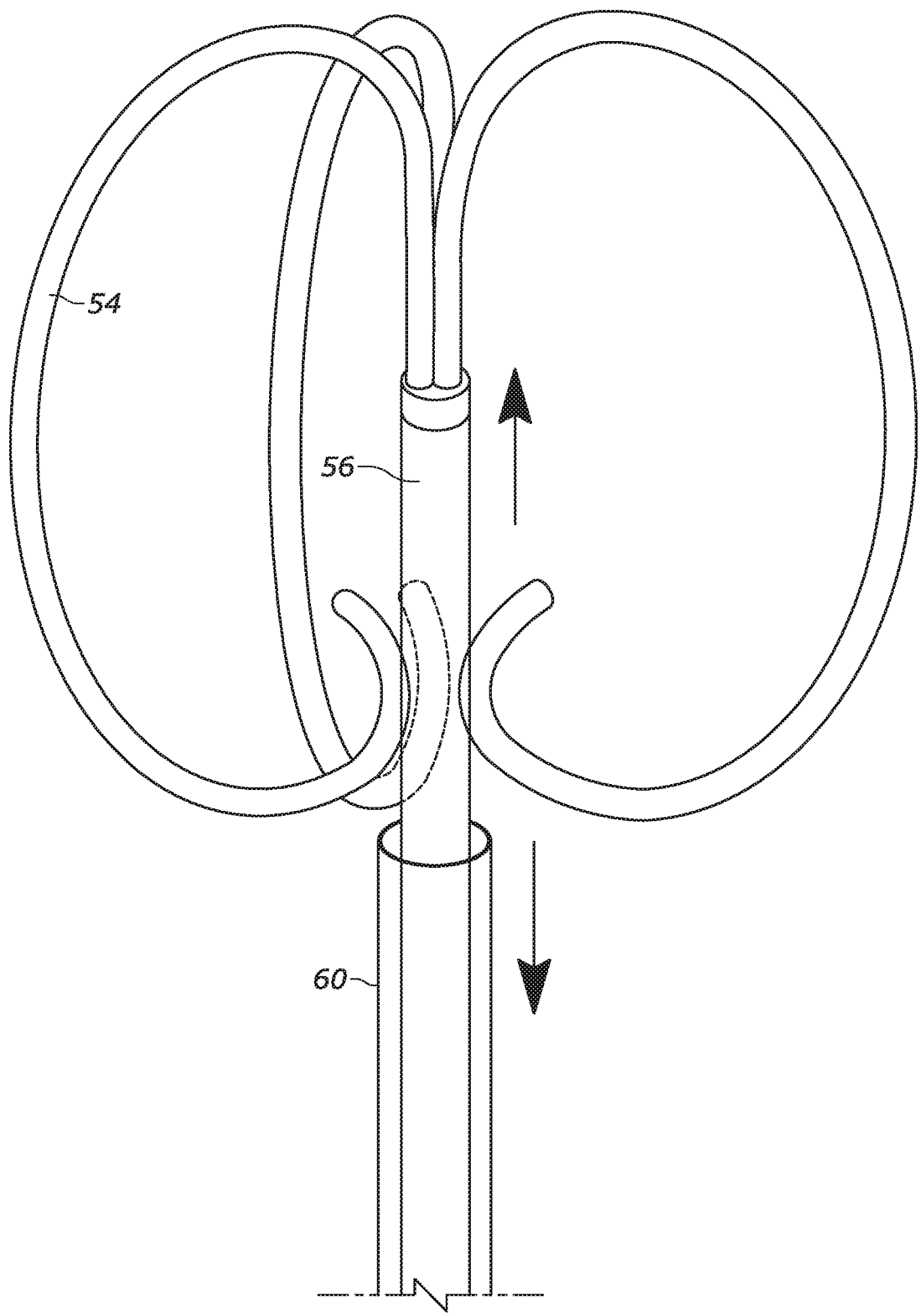

FIGS. 8A-8C schematically illustrate exemplary steps of a method of delivering an embolization system into a blood vessel using a "pull-push" approach. An embolization scaffold device 54 is releasably coupled to the distal end of a pusher 56 in an unexpanded configuration and inserted into a lumen 58 of a microcatheter 60 as depicted in FIG. 8A. Embolization scaffold device 54 is coaxial with pusher 56 in a compressed state and therefore can be delivered with a standard microcatheter into an aneurysm due to the compact nature of the scaffold in the microcatheter. Microcatheter 60 is then retracted in a proximal direction allowing embolization scaffold device 54 to "unfurl" as illustrated in FIG. 8B. When the embolization scaffold device comprises a shape memory material, the scaffold can resume its original shape after exiting the microcatheter and substantially conform to the configuration of the aneurysm. Referring to FIG. 8C, embolization scaffold device 54 can be placed in its final position by advancing pusher 56 in a distal direction and optionally further retracting microcatheter 60 in a proximal direction. The embolization scaffold device can then be detached from the pusher (e.g. electrolytically or mechanically) and an embolization coil can be delivered into the aneurysm. Alternatively, in embodiments where the embolization scaffold device is coupled to an embolization coil, the embolization coil can be advanced by the pusher or another tool into the aneurysm after the embolization scaffold device is deployed and the embolization coil can be detached from the pusher.

Figure 9A:
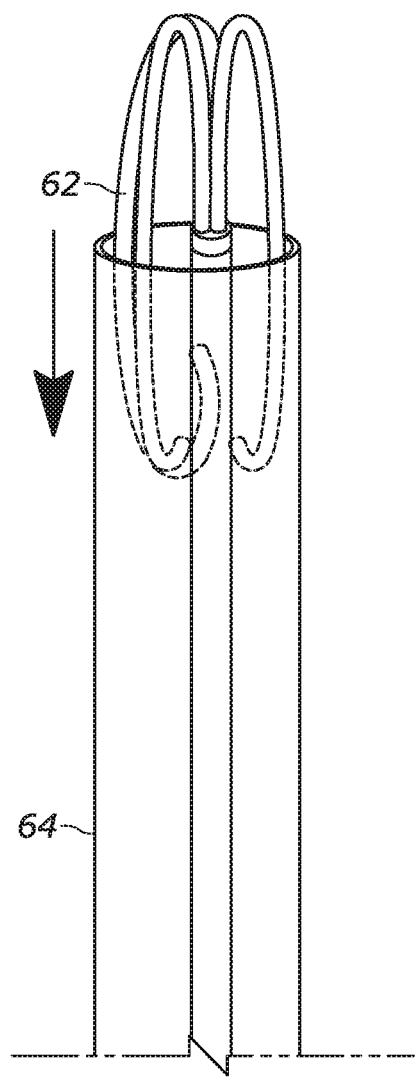
FIGS. 9A-9C are schematic illustrations depicting steps of a method of deploying an embolization scaffold device according to an embodiment of the present disclosure.
Figure 9B:
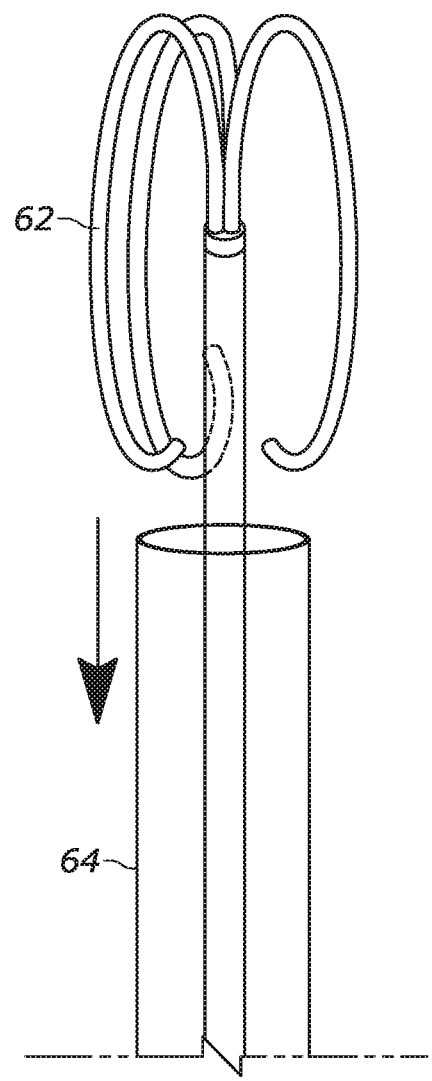
Figure 9C:
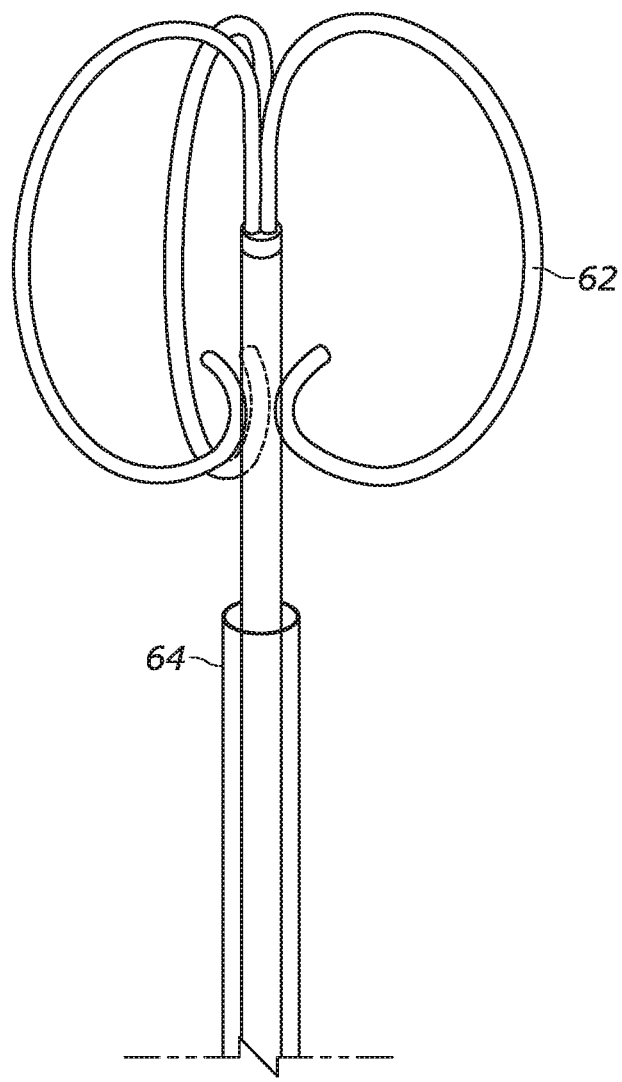

FIGS. 9A-9C depicts an alternative method of delivering an embolization scaffold device 62 which does not require a tool that pushes the device into its final position in the aneurysm. In this embodiment, embolization scaffold device 62 is delivered primarily by unsheathing a catheter 64. In particular, embolization scaffold device 62 is loaded into catheter 64 and catheter 64 is positioned within the aneurysm. Catheter 64 is slowly unsheathed (retracted proximally) as shown stepwise in FIGS. 9A-9C until embolization scaffold device 62 assumes an expanded configuration. Such an approach can allow for a gentler scaffold apposition to the aneurysm wall (e.g. less stress on the aneurysm during deployment) and can eliminate the step of pushing the embolization scaffold device into its final position.

An alternative delivery approach is to have the microcatheter positioned at the inlet of the aneurysm and have the embolization scaffold device positioned only by a 'push' mechanism on the pusher while holding the microcatheter stationary. The entire delivery and positioning of the device, in this instance, can rely on the 'memory' or the flexibility of the scaffold to allow the device to be properly unfurled within the aneurysm.

In any of the embodiments described above and particularly with respect to using a microcatheter, once the scaffold is deposited within the aneurysm, the microcatheter can remain within the aneurysm, such as an intrasaccular aneurysms, through the aneurysm treatment. This allows delivery of an integrated embolization coil that can be custom-sized to the scaffold and joined in line to the scaffold by a flexible linker as described above. Alternatively, the scaffold can be detached and an adjunctive embolization coil can be delivered without repositioning the microcatheter. This obviates the need to either re-select the aneurysm with the microcatheter (e.g. re-positioning the opening of the microcatheter back into the aneurysm in order to enable coiling) or using a secondary microcatheter to carry out the coiling of the aneurysm. This increases the speed of embolization, decreases the surgical difficulties of the aneurysm treatment, and can permit a single-step, single-device treatment of both ruptured and unruptured broad-based aneurysms without the need for dual anti-platelet therapy. The above methods are exemplary and other methods of delivering an embolization scaffold device or system can be employed.

Figure 10:
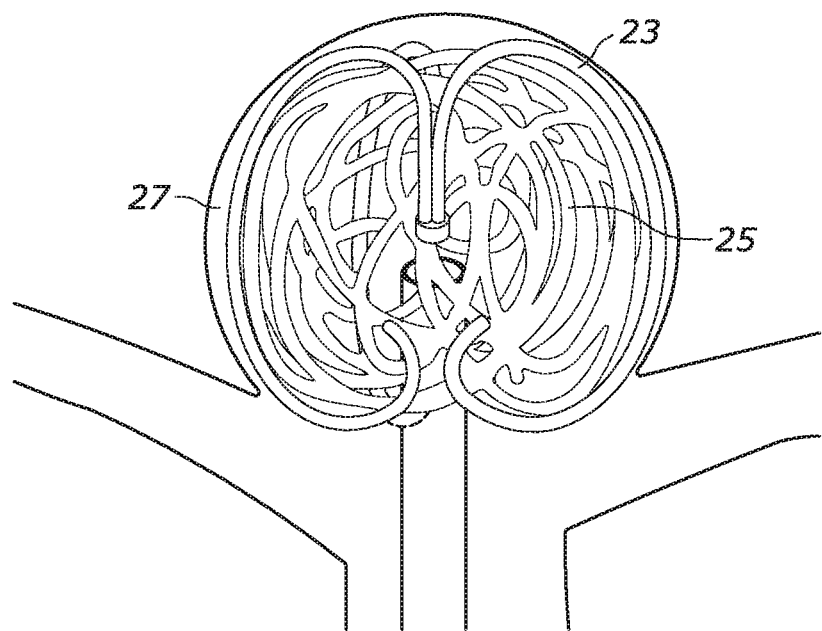
FIG. 10 is a perspective view of an embolization scaffold device and embolization coil disposed in a saccular aneurysm according to an embodiment of the present disclosure.

Methods and devices as disclosed herein can be used to occlude blood vessels to artificially create an embolus such as occluding an aneurysm or vascular malformation emerging from a blood vessel, whilst preserving patency of the parent vessel or deliberately occluding the associated artery or vein. Such method and devices can be used to treat aneurysms located throughout the body, including, but not limited to cerebral aneurysms, carotid aneurysms, thoracic aortic aneurysms, abdominal aortic aneurysms, popliteal artery aneurysms, coronary artery aneurysms, splenic artery aneurysms, celiac artery aneurysms, and mycotic aneurysms. The aneurysms can have different morphologies. For example, the aneurysm can be saccular, broad-based or fusiform. FIG. 10 illustrates an embolization coil 25 retained in position at least partially within an embolization scaffold device 23 in a saccular aneurysm 27 and FIG. 2 illustrates an embolization coil 17 retained in position at least partially within an embolization scaffold device 21 in a broad-based aneurysm 19. Methods and devices can also be used to treat, for example, tumors or vascular malformations, such as arteriovenous malformations, Vein of Galen malformations and other cerebral vascular malformations, fistulas, and other vascular malformation, blood vessel pathologies or abnormalities. In a deconstructive approach, methods and devices can be used for venous or arterial blood vessel occlusion and sacrifice.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. An embolization scaffold device having a non-deployed configuration and a deployed, expanded configuration, the device comprising:
a plurality of expandable struts each having:
a base having a central longitudinal axis extending therethrough;
a proximal portion extending from the base and substantially aligned with the central longitudinal axis;
an intermediate arcuate portion radially extending away from the central longitudinal axis and configured to applying radial outward force against an inner surface of a wall of an aneurysm in a deployed, expanded configuration, the intermediate arcuate portion being longer than the base and the proximal portion; and
a distal portion curving back towards the central longitudinal axis and providing a scaffold coverage at the neck of the aneurysm in the deployed, expanded configuration.

2. The embolization scaffold device of claim 1, wherein each of the plurality of struts has a distal end curving away from the central longitudinal axis towards the intermediate arcuate portion.

3. The embolization scaffold device of claim 1 wherein the plurality of struts comprises three struts arranged circumferentially about the central longitudinal axis of the base.

4. The embolization scaffold device of claim 1, wherein the plurality of struts comprises a first set of struts and a second set of struts, the second set of struts located proximal to the first set of struts.

5. The embolization scaffold device of claim 1, wherein at least one of the plurality of struts further comprises a tine located at a distal end of the at least one of the plurality of struts, the tine oriented in a direction away from the central longitudinal axis of the base.

6. The embolization scaffold device of claim 5, wherein the at least one of the plurality of struts comprises a first strut and an opposing second strut, the first and second opposing strut each having a tine oriented in a direction away from the central axis of the base.

7. An embolization kit comprising:
an embolization scaffold device having a non-deployed configuration and a deployed, expanded configuration, the device comprising:
a base having a central longitudinal axis extending therethrough;
a plurality of expandable struts each having:
a base having a central longitudinal axis extending therethrough;
a proximal portion extending from the base and substantially aligned with the central longitudinal axis;
an intermediate arcuate portion radially extending away from the central longitudinal axis and configured to applying radial outward force against an inner surface of a wall of an aneurysm in a deployed, expanded configuration, the intermediate arcuate portion being longer than the base and the proximal portion; and
a distal portion curving back towards the central longitudinal axis and providing a scaffold coverage at the neck of the aneurysm in the deployed, expanded configuration; and
an embolization coil.

8. An embolization system comprising:
an embolization scaffold device having a non-deployed configuration and a deployed, expanded configuration, the device comprising:
a plurality of expandable struts each having:
a base having a central longitudinal axis extending therethrough;
a proximal portion extending from the base and substantially aligned with the central longitudinal axis;
an intermediate arcuate portion radially extending away from the central longitudinal axis and configured to applying radial outward force against an inner surface of a wall of an aneurysm in a deployed, expanded configuration, the intermediate arcuate portion being longer than the base and the proximal portion; and a distal portion curving back towards the central longitudinal axis and providing a scaffold coverage at the neck of the aneurysm in the deployed, expanded configuration; and an embolization coil connected to the embolization scaffold device.

9. The embolization system of claim 8, wherein the embolization coil is connected to the embolization scaffold device via a flexible linker.

10. The embolization scaffold device of claim 1, wherein the base is wholly contained within the plurality of expandable struts.

11. A method of delivering an embolization system into an aneurysm comprising:

inserting the embolization scaffold device of claim 1 in an unexpanded configuration into a lumen of a catheter having a distal end positioning a distal end of the catheter adjacent to an aneurysm; and deploying the embolization scaffold device into the aneurysm whereby the embolization scaffold device assumes an expanded configuration.

12. The method of claim 11, wherein deploying the embolization scaffold device into the aneurysm comprises pulling the catheter in a proximal direction to expose the embolization scaffold device and pushing the embolization scaffold device in a distal direction via a pusher wire disposed in the lumen of the catheter.

13. The method of claim 12, further comprising inserting a coil into the lumen of the catheter and deploying the coil into the aneurysm, the coil retained in position at least partially within the embolization scaffold device.

* * * * *